United States Patent [19]

Ogawa et al.

[11] 4,088,822
[45] May 9, 1978

[54] SIMULTANEOUS PRODUCTION OF METHACRYLIC ACID AND A METHACRYLATE OR ACRYLIC ACID AND AN ACRYLATE

[75] Inventors: Masanobu Ogawa; Toshitake Kojima, both of Takasaki, Japan

[73] Assignee: Nippon Kayaku Kabushiki Kaisha, Tokyo, Japan

[21] Appl. No.: 688,916

[22] Filed: May 21, 1976

[30] Foreign Application Priority Data

Jun. 2, 1975 Japan .................................. 50-66343
Jun. 2, 1975 Japan .................................. 50-66344

[51] Int. Cl.$^2$ ............................................ C07C 69/54
[52] U.S. Cl. .................................... 560/207; 560/232; 260/530 N; 252/437
[58] Field of Search ............... 260/486 R, 494, 530 N

[56] References Cited

U.S. PATENT DOCUMENTS 3,772,381  11/1973  Nakamura et al. ............... 260/486 R
3,976,688  8/1976  Akiyama et al. ................. 260/530 N

FOREIGN PATENT DOCUMENTS 1,054,132  1/1967  United Kingdom ............ 260/530 N Primary Examiner—Paul J. Killos
Attorney, Agent, or Firm—Russell & Nields

[57] ABSTRACT

Methacrylic acid and its ester or acrylic acid and its ester are prepared at the same time by reacting methacrolein or acrolein with an aliphatic alcohol and molecular oxygen in vapor phase in the presence of a Pd — P — O or Pd — P — Sb — O catalyst.

12 Claims, No Drawings

SIMULTANEOUS PRODUCTION OF METHACRYLIC ACID AND A METHACRYLATE OR ACRYLIC ACID AND AN ACRYLATE

This invention relates to a process for producing methacrylic acid and a methacrylate or acrylic acid and an acrylate at the same time.

More particularly, this invention relates to a process for simultaneously producing methacrylic acid and a methacrylate or acrylic acid and an acrylate which comprises reacting methacrolein or acrolein with an aliphatic alcohol and molecular oxygen in vapor phase in the presence of a catalyst which contains palladium, phosphorus and oxygen as essential elements and antimony as an optional element.

The process of the invention may further comprise supplying into the reaction system a phosphoric acid or a phosphorus compound capable of forming a phosphoric acid through chemical change during the reaction.

For the synthesis of methacrylic acid by oxidizing methacrolein in vapor phase a number of catalysts have hitherto been proposed.

Almost all of these catalysts, however, have low activities. Further, if the reaction is carried out at elevated temperatures in order to increase the rate of reaction, large amounts of undesirable by-products such as carbon monoxide, carbon dioxide, etc. are produced so that the per-pass yield of methacrylic acid is very low.

The catalysts as disclosed in Japanese Patent Laid-Open Publication Nos. 67216/1973 and 61416/1973, which are improved in their catalytic activity and selectivity, comprise phosphomolybdic acid or its salts as a main ingredient.

The phosphomolybdic catalyst has serious disadvantages in that it is short in service life and thermally unstable so that the catalytic activity starts to rapidly decrease at a reaction or calcining temperature of more than 450° C. Once the catalyst has deteriorated, it can be regenerated no more by a simple treatment, for example, by calcining it again. These facts show that the phosphomolybdic catalyst is not always available for commercial use.

Further, when the reaction is to be carried out at high space velocities, the phosphomolybdic catalyst will serve only for a short period.

Japanese Patent Laid-Open Publication No. 30,826/1975 discloses a process for producing methyl methacrylate comprising reacting methacrolein with methanol and oxygen in the presence of a molybdenum-vanadium-tungsten series catalyst. The process is far from commercially satisfactory due to the very low yield of methyl methacrylate.

Another disclosure relating to a catalyst containing palladium, phosphorus and oxygen is described in Japanese Patent Laid-Open Publication No. 37,719/1975. Methacrylic acid is prepared by oxidizing methacrolein with molecular oxygen in the presence of the above catalyst. The destined product, methacrylic acid is produced in higher yield and selectivity, while a comparatively large amount of water vapor is required. The larger the feed, the larger the equipment, which is undesirable on an industrial scale and economically disadvantageous. Since the process of the above application is only directed to the preparation of methacrylic acid, it is, of course, impossible to prepare an ester or methacrylate at the same time.

The inventors made precise investigations to obviate the above described drawbacks and have achieved the invention.

According to the present invention, methacrolein or acrolein is susceptible to oxidation at low temperatures and methacrylic acid and a methacrylate or acrylic acid and an acrylate are produced in high yields at the same time. Further the formation of by-products such as acetic acid, carbon monoxide and carbon dioxide owing to the degradation is well suppressed. The amount of water vapor to be fed during the reaction may be very small, which is one of the important characteristics of the invention. In addition the catalyst according to the present invention is thermally stable and therefore has a substantially longer service life, particularly even when the reaction is carried out at high space velocities.

The process of the invention is not only economically advantageous, but also industrially epoch-making.

The catalyst to be used in the present invention is a composition consisting of (1) palladium, (2) phosphorus and (3) oxygen as essential elements and (4) antimony as an optional element and has a long service life which is significantly superior to those of the prior phosphomolybdic catalysts.

It has surprisingly been found that the catalyst used herein is stable at elevated temperatures, for example, at 600° C.

However, this catalyst as such is not completely satisfactory, because a part of phosphorus which is one of the essential components of the catalyst, though in a very small amount, leaves the catalyst system during the reaction. Consequently, the semi-eternal life required for commercial catalysts can not be attained.

The inventors have found that when the reaction is carried out in the presence of the catalyst, the catalyst can be stabilized and its service life can further be prolonged by continuously or intermittently supplementing phosphorus in an appropriate amount corresponding to that of the phosphorus which leaves the catalyst system.

The process of the present invention is epoch-making and of great value for commercial use because methacrylic acid and a methacrylate or acrylic acid and an acrylate can be selectively produced in high yields for long periods of time.

The term "a phosphoric acid or a phosphorus compound capable of forming a phosphoric acid through chemical change during the reaction" (hereinafter to be referred to as a phosphorus-containing compound) which is to be supplied to the reaction system in accordance with the present invention means any of phosphoric acids and phosphorus compounds capable of forming a phosphoric acid through a chemical reaction such as hydrolysis, oxidation, etc., including orthophosphoric acid, pyrophosphoric acid, metaphosphoric acid, phosphorous acid, hypophosphorus acid, phosphine, organic phosphoric acids, solid phosphoric acids, etc.

To the reaction system the phosphorus-containing compound may be supplied in any suitable manner.

For example, if the phosphorus-containing compound is water-soluble, it may uniformly be dissolved in water and an aliphatic alcohol to be used for the reaction so that it is carried to the reaction system along with water.

If the phosphorus-containing compound is solid, for example, a solid phosphoric acid, this solid material may be charged in front of the catalyst layer. As water vapor is fed and makes contact with the charged material, the latter generates a phosphoric acid, which is carried to the catalyst layer along with water vapor.

Furthermore, if the phosphorus-containing compound is gaseous, a gaseous mixture of the same and air may be fed to the catalyst layer.

The amount of the phosphorus-containing compound to be supplied may vary over a wide range. In general, the phosphorus-containing compound is supplied so that the amount of phosphorus cntained in the compound is preferably 5 to $1 \times 10^{-4}$ wt%, more particularly 0.5 to $1 \times 10^{-3}$ wt% on the basis of a total amount of water and an aliphatic alcohol fed during the reaction.

A preferred catalyst according to the present invention is a composition represented by the following formula:

$$Pd_aP_bSb_cO_d$$

in which letters $a$, $b$, $c$, and $d$ represent numbers of palladium, phosphorus, antimony and oxygen atoms, respectively, preferably when $a$ is 1, $b$ is 1 to 42, $c$ is 0 to 15, and $d$ is a number which is of itself determined by total valences of other elements, generally from 3.5 to 115.

A more preferred catalyst is a composition represented by the above formula in which the ratio between $a$, $b$, $c$ and $d$ lies in the following range:

$$a:b:c:d = 1:(1-28):(0.2-10):(3.8-85)$$

The catalyst according to the present invention can be prepared in a conventional manner well known in the art, for example, by the following procedures.

In one case, compounds of respective constituent elements and the carrier, if a carrier is used, are mixed. The resultant solution is evaporated to dryness and then the dried product is calcined.

In another case, a solid carrier is impregnated with compounds of respective constituent elements. This impregnated carrier is subjected to evaporation to dryness and then calcined.

In yet another case, a solid carrier is impregnated with compounds of some constituent elements and then subjected to a heat treatment, preferably at a temperature of 100°– 800° C. The partly impregnated carrier is further impregnated with compounds of the remaining constituent elements. This twice impregnated carrier is subjected to evaporation to dryness and then calcined.

In any of the above-described procedures the calcining temperature lies preferably in the range of 300° – 800° C, more preferably in the range of 350° – 550° C.

Examples of compounds of respective constituent elements are listed below.

Specific examples of palladium compounds include palladium chloride, nitrate and sulfate, palladium black and the like.

Specific examples of phosphorus compounds include orthophosphoric, pyrophosphoric, metaphosphoric, polyphosphoric, phosphorus and hypophosphorous acids and salts thereof and the like.

Specific examples of antimony compounds include oxides, hydroxides and chlorides of antimony such as antimony trioxide, trichloride and pentachloride and the like.

It is preferred to use a carrier for the catalyst, because the carrier makes it possible to lower the concentration of the catalyst, enhance the catalytic action and achieve catalyst economy.

As the carrier may be employed inert substances such as silica sol, silica gel, silicon carbide, $\alpha$-alumina, celite, boiling bubble stone, aluminum powder and the like.

The aliphatic alcohol used herein is, for example, methanol, ethanol and the like.

Molecular oxygen is used for oxidizing methacrolein or acrolein in accordance with the present invention. To this end air is generally used. Pure oxygen may also be used alone or in admixture with an inert gas such as nitrogen, carbon dioxide and the like.

To the reaction system methacrolein or acrolein and oxygen are fed as a gaseous feed mixture in such proportions that the molar ratio of methacrolein or acrolein to oxygen is preferably 1 : (0.5 – 30), more preferably 1 : (1 – 8).

If an aliphatic alcohol is absent in the reaction system using the catalyst according to the present invention, the oxidation of methacrolein or acrolein with molecular oxygen should be carried out in the presence of water vapor to prepare methacrylic acid or acrylic acid. The presence of water vapor is indispensable to this reaction. If water vapor is not fed, the oxidation of methacrolein or acrolein may take place to a very small extent or may not occur at all. The process of the invention, however, involves feeding of an aliphatic alcohol to the reaction system. The coexistence of the aliphatic alcohol permits to obtain the aimed products without feeding water vapor. That is, methacrylic acid and a methacrylate or acrylic acid and an acrylate can be obtained in sufficiently high yield and selectivity in the absence of water vapor. It may be understood that the addition of a small amount of water vapor can further increase the conversion of methacrolein or acrolein and hence the yield of methacrylic acid and methacrylate or acrylic acid and an acrylate produced.

The water vapor is added in the gaseous feed mixture in such proportions that the amount of water vapor is preferably 0.1 to 28 moles, more preferably 0.5 to 10 moles per mole of methacrolein or acrolein.

The aliphatic alcohol is preferably fed in an amount from 0.1 to 25 moles, especially 0.3 to 10 moles per mole of methacrolein or acrolein.

The temperature for carrying out the reaction is not so critical. The reaction may preferably be carried out at a temperature of 180° to 370° C, especially 210° to 350° C.

The reaction can be carried out at atmospheric pressure or at lower or higher pressures. In general it is convenient to carry out the reaction at atmospheric pressure. A preferable range of pressure is 0.3 to 15 atm.

The gaseous feed mixture can be introduced at any desirable space velocity, preferably at a space velocity of 300 to 15,000 1-gas/1-cat. hr, especially 700 to 8,000 1-gas/1-cat. hr.

According to the present invention satisfactory results are obtained even when the reaction is carried out at space velocities as high as 2,000 to 8,000 1-gas/1-cat. hr. Further the service life of the catalyst is maintained for a long period of time under such conditions.

The catalyst of the present invention may be applied in any form selected from a fixed bed, a fluidized bed and a moving bed.

The following examples are illustrative of the catalyst and the process of the present invention. In the examples the terms "conversion of methacrolein or acrolein", "selectivity of methacrylic or acrylic acid", "selectivity of a methacrylate or acrylate", "yield of methacrylic or acrylic acid", "yield of a methacrylate or acrylate", and "space velocity" are defined as follows.

Conversion of methacrolein or acrolein =

$$\frac{\text{The number of moles of reacted methacrolein or acrolein}}{\text{The number of moles of fed methacrolein or acrolein}} \times 100\%$$

Selectivity of methacrylic or acrylic acid =

$$\frac{\text{The number of moles of produced methacrylic or acrylic acid}}{\text{The number of moles of reacted methacrolein or acrolein}} \times 100\%$$

Selectivity of a methacrylate or acrylate =

$$\frac{\text{The number of moles of produced methacrylate or acrylate}}{\text{The number of moles of reacted methacrolein or acrolein}} \times 100\%$$

Yield of methacrylic or acrylic acid =

$$\frac{\text{The number of moles of produced methacrylic or acrylic acid}}{\text{The number of moles of fed methacrolein or acrolein}} \times 100\%$$

Yield of a methacrylate or acrylate =

$$\frac{\text{The number of moles of produced methacrylate or acrylate}}{\text{The number of moles of fed methacrolein or acrolein}} \times 100\%$$

Space Velocity (SV) =

$$\frac{\text{The flow rate* of a gaseous feed mixture } (\frac{\text{l-gas}}{\text{Hr.}})}{\text{The volume of a charged catalyst (l-cat.)}}$$

*calculated on a basis at the normal temperature and pressure

EXAMPLE 1

With heating and stirring to 115.8 g of silica sol was added 0.71 g of antimony trioxide. This mixture was heated to concentrate the same, evaporated to dryness and then dried at 270° C for eight hours. The product was impregnated with aqueous ammonia containing 0.9 g of palladium chloride and then evaporated to dryness. After the dried product was repeatedly washed with distilled water (the total amount is 10 l) and dried, it was further impregnated with 5.4 g of hypophosphorous acid, evaporated to dryness and then dried at 270° C for another eight hours. The dried product was calcined in the air at 450° C for four hours. The thus obtained product is named Catalyst A, the composition of which is represented by the formula:

$$Pd_1P_5Sb_1O_{15}$$

A reaction tube of stainless steel having an inner diameter of 20 mm was filled with 10 ml of Catalyst A and dipped in a bath of molten nitrate. With the use of this reaction tube filled with Catalyst A the oxidation of methacrolein was carried out for 90 days.

A gaseous feed mixture contained methacrolein, methanol, oxygen, water vapor and nitrogen in a relative molar ratio of 1 : 1 : 4 : 1 : 16.1 and was supplied at a SV of 1034 hr$^{-1}$.

The results are shown in Table 2. On the production of methacrylic acid and methyl methacrylate from methacrolein small amounts of by-products were derived, in which were included 3.0% of acrylic acid, 1.1% of acetic acid, 3.5% of carbon dioxide and 4.0% of carbon monoxide at a reaction time of 0 day.

EXAMPLES 2 - 6

Catalysts B - F each consisting of the composition shown in Table 1 were prepared in accordance with the procedures described in Example 1, respectively. With the use of each catalyst the reaction was carried out in a similar manner as described in Example 1. The results are shown in Table 2.

EXAMPLE 7

Silica sol (115.8 g) was concentrated with heating and stirring, evaporated to dryness and then dried at 270° C for eight hours. The dried product was impregnated with aqueous ammonia containing 0.9 g of palladium chloride and then evaporated to dryness. After the dried product was repeatedly washed with distilled water (a total amount is 10 l) and dried, it was further impregnated with 5.4 g of hypophosphorous acid, evaporated to dryness and then dried at 270° C for another eight hours. The dried product was calcined in the air at 450° C for four hours. The thus obtained product is named Catalyst G, the composition of which is represented by the formula:

$$Pd_1P_5O_{13.5}$$

With the use of Catalyst G the oxidation of methacrolein was carried out in a similar maner as in Example 1. The results are shown in Table 2.

On the production of methacrylic acid and methyl methacrylate from methacrolein at a space velocity (SV) of 1034 hr$^{-1}$ small amounts of by-products including 2.5% of acrylic acid, 1.5% of acetic acid, 3.7% of carbon dioxide and 4.1% of carbon monoxide were derived at a reaction time of 0 day.

EXAMPLES 8 - 11

Catalysts H - K each consisting of the composition shown in Table 1 were prepared in accordance with the procedures described in Example 7. With the use of each catalyst the reaction was carried out in a similar manner as described in Example 1. The results are shown in Table 2.

Table 1

| Example | Composition of Catalyst | | | | |
|---|---|---|---|---|---|
| | Pd | P | Sb | O | |
| 1 | 1 | 5 | 1 | 15 | Catalyst A |
| 2 | 1 | 1 | 0.5 | 4.25 | Catalyst B |
| 3 | 1 | 10 | 1 | 27.5 | Catalyst C |
| 4 | 1 | 15 | 1 | 40 | Catalyst D |
| 5 | 1 | 20 | 2.5 | 54.75 | Catalyst E |
| 6 | 1 | 5 | 7 | 24 | Catalyst F |
| 7 | 1 | 5 | — | 13.5 | Catalyst G |
| 8 | 1 | 2 | — | 6 | Catalyst H |
| 9 | 1 | 12 | — | 31 | Catalyst I |
| 10 | 1 | 15 | — | 38.5 | Catalyst J |
| 11 | 1 | 20 | — | 51 | Catalyst K |

Table 2

| Example | Catalyst | Reaction time (day) | SV (hr$^{-1}$) | Temperature of the nitrate bath (° C) | Conversion of methacrolein (%) | Yield of methacrylic acid (%) | Yield of methyl methacrylate (%) | Selectivity of methacrylic acid + methyl methacrylate (%) |
|---|---|---|---|---|---|---|---|---|
| 1 | A | 0 | 1034 | 300 | 73.3 | 29.5 | 32.7 | 84.9 |
|   |   | 0 | 4000 | 315 | 69.4 | 27.0 | 30.2 | 82.5 |
|   |   | 60 | 4000 | 315 | 62.1 | 22.9 | 28.2 | 82.3 |
|   |   | 90 | 4000 | 315 | 60.3 | 23.0 | 26.5 | 82.1 |
| 2 | B | 0 | 1034 | 250 | 75.1 | 26.7 | 28.8 | 73.9 |
|   |   | 0 | 4000 | 265 | 70.1 | 24.2 | 26.3 | 72.1 |
|   |   | 60 | 4000 | 265 | 64.2 | 21.7 | 23.9 | 71.1 |
|   |   | 90 | 4000 | 265 | 58.0 | 18.5 | 22.6 | 70.9 |
| 3 | C | 0 | 1034 | 313 | 75.0 | 29.8 | 31.3 | 81.5 |
|   |   | 0 | 4000 | 324 | 69.0 | 27.7 | 28.0 | 80.7 |
|   |   | 60 | 4000 | 324 | 60.1 | 24.4 | 24.0 | 80.5 |
|   |   | 90 | 4000 | 324 | 58.3 | 23.8 | 23.1 | 80.4 |
| 4 | D | 0 | 1034 | 321 | 69.1 | 29.6 | 28.7 | 84.3 |
|   |   | 0 | 4000 | 335 | 62.0 | 26.1 | 25.5 | 83.3 |
|   |   | 60 | 4000 | 335 | 57.5 | 24.3 | 23.1 | 82.5 |
|   |   | 90 | 4000 | 335 | 55.4 | 23.0 | 21.6 | 82.3 |
| 5 | E | 0 | 1034 | 326 | 69.4 | 28.5 | 28.1 | 81.5 |
|   |   | 0 | 4000 | 337 | 61.5 | 25.4 | 24.0 | 80.4 |
|   |   | 60 | 4000 | 337 | 56.1 | 23.4 | 21.5 | 80.0 |
|   |   | 90 | 4000 | 337 | 53.7 | 22.9 | 20.0 | 79.8 |
| 6 | F | 0 | 1034 | 280 | 73.0 | 28.5 | 30.1 | 80.3 |
|   |   | 0 | 4000 | 296 | 68.1 | 26.7 | 27.4 | 79.5 |
|   |   | 60 | 4000 | 296 | 63.1 | 24.2 | 25.8 | 79.2 |
|   |   | 90 | 4000 | 296 | 59.3 | 22.7 | 24.0 | 78.7 |
| 7 | G | 0 | 1034 | 302 | 71.0 | 29.0 | 30.5 | 83.8 |
|   |   | 0 | 4000 | 316 | 67.1 | 27.5 | 27.2 | 81.5 |
|   |   | 60 | 4000 | 316 | 59.5 | 24.7 | 23.5 | 81.0 |
|   |   | 90 | 4000 | 316 | 54.3 | 22.6 | 21.2 | 80.7 |
| 8 | H | 0 | 1034 | 280 | 73.4 | 29.6 | 29.9 | 81.1 |
|   |   | 0 | 4000 | 295 | 68.5 | 27.2 | 27.9 | 80.5 |
|   |   | 60 | 4000 | 295 | 63.2 | 24.9 | 25.7 | 80.0 |
|   |   | 90 | 4000 | 295 | 58.1 | 22.7 | 23.5 | 79.5 |
| 9 | I | 0 | 1034 | 307 | 70.0 | 28.1 | 30.0 | 83.0 |
|   |   | 0 | 4000 | 319 | 62.3 | 26.2 | 25.0 | 82.1 |
|   |   | 60 | 4000 | 319 | 56.1 | 23.5 | 22.3 | 81.6 |
|   |   | 90 | 4000 | 319 | 51.5 | 22.2 | 19.2 | 80.3 |
| 10 | J | 0 | 1034 | 311 | 69.5 | 28.1 | 29.4 | 82.7 |
|   |   | 0 | 4000 | 326 | 61.3 | 25.0 | 25.5 | 82.4 |
|   |   | 60 | 4000 | 326 | 53.4 | 22.3 | 21.1 | 81.3 |
|   |   | 90 | 4000 | 326 | 46.1 | 20.1 | 17.0 | 80.5 |
| 11 | K | 0 | 1034 | 321 | 58.3 | 22.4 | 23.4 | 78.6 |
|   |   | 0 | 4000 | 337 | 51.2 | 20.2 | 19.3 | 77.1 |
|   |   | 60 | 4000 | 337 | 43.1 | 17.3 | 15.5 | 76.0 |
|   |   | 90 | 4000 | 337 | 36.2 | 15.3 | 12.0 | 75.4 |

EXAMPLES 12 – 22

The reaction described in Example 1 was repeated in the presence of Catalysts A – K, respectively, except that acrolein was used in place of methacrolein. A gaseous feed mixture contained acrolein, methanol, oxygen, water vapor and nitrogen in a relative molar ratio of 1 : 1 : 2 : 3 : 8. The results are shown in Table 3.

Table 3

| Example | Catalyst | Reaction time (day) | SV (hr$^{-1}$) | Temperature of the nitrate bath (° C) | Conversion of acrolein (%) | Yield of acrylic acid (%) | Yield of methyl acrylate (%) | Selectivity of acrylic acid + methyl acrylate (%) |
|---|---|---|---|---|---|---|---|---|
| 12 | A | 0 | 1309 | 290 | 96.5 | 65.5 | 27.0 | 95.9 |
|   |   | 0 | 4000 | 304 | 91.3 | 61.0 | 25.5 | 94.7 |
|   |   | 60 | 4000 | 304 | 85.1 | 56.1 | 23.7 | 93.8 |
|   |   | 90 | 4000 | 304 | 81.5 | 55.0 | 21.1 | 93.4 |
| 13 | B | 0 | 1309 | 250 | 94.1 | 60.1 | 23.6 | 88.9 |
|   |   | 0 | 4000 | 266 | 89.0 | 58.2 | 19.9 | 87.8 |
|   |   | 60 | 4000 | 266 | 83.1 | 54.3 | 17.7 | 86.7 |
|   |   | 90 | 4000 | 266 | 76.2 | 50.2 | 14.6 | 85.1 |
| 14 | C | 0 | 1309 | 309 | 94.2 | 64.4 | 25.1 | 95.0 |
|   |   | 0 | 4000 | 323 | 90.1 | 61.6 | 23.5 | 93.9 |
|   |   | 60 | 4000 | 323 | 83.2 | 55.4 | 21.2 | 92.1 |
|   |   | 90 | 4000 | 323 | 79.3 | 54.5 | 17.5 | 90.8 |
| 15 | D | 0 | 1309 | 318 | 92.1 | 64.2 | 21.5 | 93.1 |
|   |   | 0 | 4000 | 322 | 84.7 | 58.2 | 19.7 | 92.0 |
|   |   | 60 | 4000 | 322 | 78.1 | 54.4 | 16.8 | 91.2 |
|   |   | 90 | 4000 | 322 | 73.0 | 53.1 | 13.0 | 90.6 |

Table 3-continued

| Example | Catalyst | Reaction time (day) | SV (hr$^{-1}$) | Temperature of the nitrate bath (° C) | Conversion of acrolein (%) | Yield of acrylic acid (%) | Yield of methyl acrylate (%) | Selectivity of acrylic acid + methyl acrylate (%) |
|---|---|---|---|---|---|---|---|---|
| 16 | E | 0 | 1309 | 321 | 91.6 | 55.0 | 21.1 | 83.1 |
|    |   | 0 | 4000 | 335 | 82.3 | 50.2 | 17.3 | 82.0 |
|    |   | 60 | 4000 | 335 | 74.1 | 46.3 | 13.8 | 81.1 |
|    |   | 90 | 4000 | 335 | 69.8 | 44.0 | 12.4 | 80.8 |
| 17 | F | 0 | 1309 | 281 | 96.7 | 61.7 | 23.5 | 88.1 |
|    |   | 0 | 4000 | 294 | 88.8 | 54.9 | 21.0 | 85.5 |
|    |   | 60 | 4000 | 294 | 82.4 | 51.1 | 18.3 | 84.2 |
|    |   | 90 | 4000 | 294 | 77.6 | 49.5 | 15.1 | 83.2 |
| 18 | G | 0 | 1309 | 300 | 96.7 | 64.3 | 27.0 | 94.4 |
|    |   | 0 | 4000 | 313 | 90.3 | 62.0 | 22.1 | 93.1 |
|    |   | 60 | 4000 | 313 | 83.1 | 57.0 | 20.0 | 92.6 |
|    |   | 90 | 4000 | 313 | 77.5 | 53.2 | 18.0 | 91.8 |
| 19 | H | 0 | 1309 | 278 | 92.1 | 60.4 | 22.8 | 90.3 |
|    |   | 0 | 4000 | 293 | 85.2 | 56.7 | 19.2 | 89.1 |
|    |   | 60 | 4000 | 293 | 81.1 | 53.3 | 18.1 | 88.0 |
|    |   | 90 | 4000 | 293 | 75.4 | 50.2 | 15.5 | 87.2 |
| 20 | I | 0 | 1309 | 310 | 95.4 | 64.3 | 22.2 | 90.7 |
|    |   | 0 | 4000 | 317 | 87.2 | 57.4 | 19.7 | 88.4 |
|    |   | 60 | 4000 | 317 | 80.2 | 53.5 | 16.5 | 87.3 |
|    |   | 90 | 4000 | 317 | 71.8 | 49.1 | 13.0 | 86.5 |
| 21 | J | 0 | 1309 | 315 | 92.1 | 59.9 | 21.8 | 88.7 |
|    |   | 0 | 4000 | 328 | 84.8 | 51.4 | 21.0 | 85.4 |
|    |   | 60 | 4000 | 328 | 77.3 | 45.2 | 20.3 | 84.7 |
|    |   | 90 | 4000 | 328 | 71.1 | 42.3 | 17.5 | 84.1 |
| 22 | K | 0 | 1309 | 328 | 88.5 | 53.4 | 18.5 | 81.2 |
|    |   | 0 | 4000 | 340 | 81.3 | 50.3 | 15.0 | 80.3 |
|    |   | 60 | 4000 | 340 | 75.1 | 45.3 | 12.6 | 77.1 |
|    |   | 90 | 4000 | 340 | 67.0 | 41.1 | 10.0 | 76.3 |

EXAMPLES 23 – 27

The reaction described in Example 1 was repeated in the presence of Catalyst A or G with a varying molar ratio between reagents in the gaseous feed mixture. The results are shown in Table 4.

In Table 4, gaseous feed mixtures L – O have the following relative molar ratio:

| Gaseous feed mixture | methacrolein | methanol | oxygen | water vapor | nitrogen |
|---|---|---|---|---|---|
| L | 1 | 2 | 4 | 0 | 16.1 |
| M | 1 | 1 | 4 | 6 | 16.1 |
| N | 1 | 1 | 2 | 4 | 8 |
| O | 1 | 1 | 2 | 14 | 16.1 |

EXAMPLES 28 – 32

The reaction described in Example 12 was repeated in the presence of Catalyst A or G with a varying molar ratio between reagents in the gaseous feed mixture. The results are shown in Table 5.

In Table 5, gaseous feed mixtures P – S have the following relative molar ratio:

| Gaseous feed mixture | acrolein | methanol | oxygen | water vapor | nitrogen |
|---|---|---|---|---|---|
| P | 1 | 1 | 4 | 0 | 16.1 |
| Q | 1 | 1 | 4 | 6 | 16.1 |
| R | 1 | 1 | 2 | 2 | 16.1 |
| S | 1 | 2 | 4 | 14 | 16.1 |

Table 4

| Example | Catalyst | Gaseous feed mixture | SV (hr$^{-1}$) | Temperature of the nitrate bath (° C) | Conversion of methacrolein (%) | Yield of methacrylic acid (%) | Yield of methyl methacrylate (%) | Selectivity of methacrylic acid + methyl methacrylate (%) |
|---|---|---|---|---|---|---|---|---|
| 23 | A | L | 1034 | 300 | 60.1 | 22.5 | 28.6 | 85.0 |
|    |   |   | 4000 | 315 | 53.3 | 20.3 | 24.5 | 84.1 |
| 24 | G | L | 1034 | 310 | 61.0 | 21.0 | 26.1 | 77.0 |
|    |   |   | 4000 | 324 | 54.7 | 18.1 | 23.6 | 76.2 |
| 25 | A | M | 1034 | 289 | 72.0 | 35.0 | 21.0 | 78.0 |
|    |   |   | 4000 | 300 | 68.5 | 30.1 | 22.7 | 77.0 |
| 26 | A | N | 1034 | 300 | 70.3 | 34.8 | 22.7 | 81.8 |
|    |   |   | 4000 | 313 | 63.1 | 30.2 | 20.4 | 80.2 |
| 27 | A | O | 1034 | 279 | 74.7 | 32.3 | 25.7 | 77.7 |
|    |   |   | 4000 | 293 | 69.7 | 30.5 | 22.5 | 76.1 |

Table 5

| Example | Catalyst | Gaseous feed mixture | SV (hr$^{-1}$) | Temperature of the nitrate bath (° C) | Conversion of acrolein (%) | Yield of acrylic acid (%) | Yield of methyl acrylate (%) | Selectivity of acrylic acid + methyl acrylate (%) |
|---|---|---|---|---|---|---|---|---|
| 28 | A | P | 1309 | 300 | 89.9 | 61.0 | 26.9 | 97.7 |
|    |   |   | 4000 | 316 | 81.7 | 55.3 | 23.7 | 96.7 |
| 29 | G | P | 1309 | 310 | 91.1 | 61.1 | 27.1 | 96.8 |

Table 5-continued

| Example | Catalyst | Gaseous feed mixture | SV (hr$^{-1}$) | Temperature of the nitrate bath (° C) | Conversion of acrolein (%) | Yield of acrylic acid (%) | Yield of methyl acrylate (%) | Selectivity of acrylic acid + methyl acrylate (%) |
|---|---|---|---|---|---|---|---|---|
| 30 | A | Q | 4000 | 314 | 84.5 | 57.1 | 24.1 | 96.1 |
|    |   |   | 1309 | 311 | 94.5 | 63.1 | 26.8 | 95.1 |
| 31 | A | R | 4000 | 325 | 89.2 | 60.7 | 23.0 | 93.8 |
|    |   |   | 1309 | 327 | 92.1 | 60.2 | 26.3 | 93.9 |
| 32 | A | S | 4000 | 342 | 87.9 | 57.1 | 24.8 | 93.2 |
|    |   |   | 1309 | 289 | 89.1 | 60.3 | 20.7 | 90.9 |
|    |   |   | 4000 | 299 | 85.3 | 58.1 | 18.4 | 89.7 |

EXAMPLE 33

The reaction described in Example 1 was carried out in the presence of Catalyst A, while a phosphorus-containing compound was supplied to the reaction system.

As the phosphorus-containing compound was used orthophosphoric acid in the form of a solution containing 0.15% of orthophosphoric acid in water and methanol.

A gaseous feed mixture contained methacrolein, methanol, oxygen, water vapor, nitrogen and phosphorus in a relative molar ratio of 1 : 1 : 4 : 1 : 16.1 : 14 ×0 10$^{-4}$.

The results are shown in Table 6.

EXAMPLES 34 – 43

Example 33 was repeated except that Catalysts B – K are used in place of Catalyst A, respectively.

The results are shown in Table 6.

EXAMPLE 44

Example 33 was repeated except that solid phosphoric acid (celite/phosphorus = 50/50) heat treated at 550° C was used as the phosphorus-containing compound in place of orthophosphoric acid.

On the upper side of the catalyst layer consisting of 10 cc of Catalyst A was placed 5 cc of solid phosphoric acid.

The results are shown in Table 6.

EXAMPLE 45

Example 33 was repeated except that trimethyl phosphate in the form of a solution containing 0.15% of trimethyl phosphate in water and methanol was used as the phosphorus-containing compound in place of orthophosphoric acid.

The relative molar ratio between methacrolein, methanol, oxygen, water vapor, nitrogen and phosphorus in the gaseous feed mixture is the same as that of Example 33.

The results are shown in Table 6.

Table 6

| Example | Catalyst | Reaction time (day) | SV (hr$^{-1}$) | Temperature of the nitrate bath (° C) | Conversion of methacrolein (%) | Yield of methacrylic acid (%) | Yield of methyl methacrylate (%) | Selectivity of methacrylic acid + methyl methacrylate (%) |
|---|---|---|---|---|---|---|---|---|
| 33 | A | 0 | 1034 | 300 | 73.3 | 29.5 | 32.7 | 84.9 |
|    |   | 40 | 1034 | 300 | 73.4 | 29.4 | 32.6 | 84.7 |
|    |   | 120 | 1034 | 300 | 73.4 | 29.6 | 32.8 | 84.9 |
|    |   | 0 | 4000 | 314 | 69.3 | 26.7 | 30.5 | 82.5 |
|    |   | 60 | 4000 | 314 | 68.8 | 26.3 | 30.6 | 82.7 |
|    |   | 90 | 4000 | 314 | 68.9 | 26.6 | 30.3 | 82.6 |
| 34 | B | 0 | 1034 | 251 | 75.2 | 27.0 | 28.6 | 74.0 |
|    |   | 0 | 4000 | 265 | 70.2 | 25.1 | 26.3 | 73.2 |
|    |   | 60 | 4000 | 265 | 70.1 | 25.2 | 26.2 | 73.3 |
|    |   | 90 | 4000 | 265 | 70.3 | 25.0 | 26.4 | 73.1 |
| 35 | C | 0 | 1034 | 313 | 75.0 | 29.8 | 31.3 | 81.5 |
|    |   | 0 | 4000 | 322 | 67.1 | 27.1 | 26.7 | 80.2 |
|    |   | 60 | 4000 | 322 | 67.3 | 27.2 | 26.8 | 80.3 |
|    |   | 90 | 4000 | 322 | 67.5 | 27.3 | 26.6 | 79.9 |
| 36 | D | 0 | 1034 | 321 | 69.1 | 29.6 | 28.7 | 84.3 |
|    |   | 0 | 4000 | 337 | 62.2 | 26.0 | 24.1 | 80.5 |
|    |   | 60 | 4000 | 337 | 61.9 | 25.9 | 24.2 | 81.0 |
|    |   | 90 | 4000 | 337 | 62.1 | 25.9 | 24.0 | 80.3 |
| 37 | E | 0 | 1034 | 326 | 69.4 | 28.5 | 28.1 | 81.5 |
|    |   | 0 | 4000 | 337 | 61.5 | 25.4 | 24.0 | 80.4 |
|    |   | 60 | 4000 | 337 | 61.7 | 25.5 | 24.1 | 80.5 |
|    |   | 90 | 4000 | 337 | 61.7 | 25.4 | 24.2 | 80.5 |
| 38 | F | 0 | 1034 | 281 | 73.1 | 28.6 | 30.9 | 81.4 |
|    |   | 0 | 4000 | 297 | 68.1 | 26.8 | 27.9 | 80.3 |
|    |   | 60 | 4000 | 297 | 68.0 | 26.7 | 28.0 | 80.4 |
|    |   | 90 | 4000 | 297 | 68.1 | 26.8 | 28.0 | 80.4 |
| 39 | G | 0 | 1034 | 302 | 71.0 | 29.0 | 30.5 | 83.8 |
|    |   | 40 | 1034 | 302 | 71.2 | 29.1 | 29.4 | 82.2 |
|    |   | 120 | 1034 | 302 | 71.5 | 31.1 | 29.0 | 84.1 |
| 39 | G | 0 | 4000 | 313 | 67.0 | 27.3 | 27.2 | 81.4 |
|    |   | 60 | 4000 | 313 | 67.1 | 27.0 | 27.0 | 80.5 |
|    |   | 90 | 4000 | 313 | 67.0 | 27.4 | 27.1 | 81.3 |
| 40 | H | 0 | 1034 | 280 | 73.4 | 29.8 | 30.5 | 82.2 |
|    |   | 0 | 4000 | 296 | 68.7 | 27.4 | 28.5 | 81.3 |
|    |   | 60 | 4000 | 296 | 68.5 | 27.5 | 28.3 | 81.4 |

Table 6-continued

| Example | Catalyst | Reaction time (day) | SV (hr$^{-1}$) | Temperature of the nitrate bath (° C) | Conversion of methacrolein (%) | Yield of methacrylic acid (%) | Yield of methyl methacrylate (%) | Selectivity of methacrylic acid + methyl methacrylate (%) |
|---|---|---|---|---|---|---|---|---|
|  |  | 90 | 4000 | 296 | 68.5 | 27.4 | 28.4 | 81.5 |
|  |  | 0 | 1034 | 305 | 69.8 | 28.1 | 30.0 | 83.2 |
|  |  | 0 | 4000 | 316 | 62.4 | 24.7 | 26.6 | 82.2 |
| 41 | I |  |  |  |  |  |  |  |
|  |  | 60 | 4000 | 316 | 62.5 | 24.9 | 26.3 | 82.1 |
|  |  | 90 | 4000 | 316 | 62.3 | 24.7 | 26.3 | 82.4 |
|  |  | 0 | 1034 | 313 | 70.3 | 28.5 | 29.4 | 82.4 |
|  |  | 0 | 4000 | 325 | 61.5 | 25.2 | 25.4 | 82.3 |
| 42 | J |  |  |  |  |  |  |  |
|  |  | 60 | 4000 | 325 | 61.3 | 25.0 | 25.5 | 82.3 |
|  |  | 90 | 4000 | 325 | 61.4 | 25.3 | 25.3 | 82.4 |
|  |  | 0 | 1034 | 322 | 58.5 | 22.6 | 23.3 | 78.4 |
|  |  | 0 | 4000 | 338 | 51.2 | 20.7 | 18.9 | 77.4 |
| 43 | K |  |  |  |  |  |  |  |
|  |  | 60 | 4000 | 338 | 51.0 | 21.1 | 18.5 | 77.7 |
|  |  | 90 | 4000 | 338 | 51.1 | 20.8 | 18.9 | 77.6 |
|  |  | 0 | 1034 | 300 | 73.0 | 29.3 | 31.6 | 83.4 |
| 44 | A | 40 | 1034 | 300 | 73.4 | 29.0 | 31.2 | 82.0 |
|  |  | 120 | 1034 | 300 | 73.1 | 29.1 | 30.9 | 82.1 |
|  |  | 0 | 1034 | 300 | 73.2 | 29.7 | 32.1 | 84.4 |
| 45 | A | 40 | 1034 | 300 | 72.9 | 29.8 | 32.2 | 85.1 |
|  |  | 120 | 1034 | 300 | 73.5 | 29.7 | 32.3 | 84.4 |

EXAMPLES 46 – 56

The reaction described in Example 45 was repeated in the presence of Catalysts A – K, respectively, except that acrolein is used as a starting material in place of methacrolein. As a phosphorus-containing material was supplied trimethyl phosphate, as described in Example 45.

The gaseous feed mixture contained acrolein, methanol, oxygen, water vapor, nitrogen and phosphorus in a relative molar ratio of $1 : 1 : 2 : 3 : 8 : 14 \times 10^{-4}$.

The results are shown in Table 7.

Table 7

| Example | Catalyst | Reaction time (day) | SV (hr$^{-1}$) | Temperature of the nitrate bath (° C) | Conversion of acrolein (%) | Yield of acrylic acid (%) | Yield of methyl acrylate (%) | Selectivity of acrylic acid + methyl acrylate (%) |
|---|---|---|---|---|---|---|---|---|
|  |  | 0 | 1309 | 290 | 96.5 | 65.5 | 27.0 | 95.9 |
|  |  | 40 | 1309 | 290 | 96.4 | 65.3 | 27.1 | 95.9 |
|  |  | 120 | 1309 | 290 | 97.0 | 65.4 | 27.2 | 95.5 |
| 46 | A |  |  |  |  |  |  |  |
|  |  | 0 | 4000 | 304 | 91.3 | 61.0 | 25.5 | 94.7 |
|  |  | 60 | 4000 | 304 | 91.2 | 61.1 | 25.3 | 94.6 |
|  |  | 90 | 4000 | 304 | 91.4 | 61.3 | 24.9 | 94.3 |
|  |  | 0 | 1309 | 251 | 94.3 | 60.2 | 23.7 | 89.0 |
|  |  | 0 | 4000 | 265 | 89.1 | 58.3 | 20.0 | 87.9 |
| 47 | B |  |  |  |  |  |  |  |
|  |  | 60 | 4000 | 265 | 89.3 | 58.4 | 20.0 | 87.8 |
|  |  | 90 | 4000 | 265 | 89.1 | 58.4 | 19.8 | 87.8 |
|  |  | 0 | 1309 | 309 | 94.2 | 64.4 | 25.1 | 95.0 |
|  |  | 0 | 4000 | 323 | 90.1 | 61.6 | 23.5 | 93.9 |
| 48 | C |  |  |  |  |  |  |  |
|  |  | 60 | 4000 | 323 | 89.7 | 60.5 | 23.8 | 94.0 |
|  |  | 90 | 4000 | 323 | 89.9 | 60.5 | 23.9 | 94.1 |
|  |  | 0 | 1309 | 318 | 92.1 | 64.2 | 21.5 | 93.1 |
|  |  | 0 | 4000 | 322 | 84.7 | 58.2 | 19.7 | 92.0 |
| 49 | D |  |  |  |  |  |  |  |
|  |  | 60 | 4000 | 322 | 84.7 | 58.4 | 19.4 | 91.9 |
|  |  | 90 | 4000 | 322 | 84.6 | 58.2 | 19.7 | 92.1 |
|  |  | 0 | 1309 | 321 | 91.5 | 55.1 | 21.1 | 83.3 |
|  |  | 0 | 4000 | 336 | 82.4 | 50.3 | 17.4 | 82.1 |
| 50 | E |  |  |  |  |  |  |  |
|  |  | 60 | 4000 | 336 | 82.3 | 50.2 | 17.5 | 82.2 |
|  |  | 90 | 4000 | 336 | 82.2 | 50.3 | 17.3 | 82.2 |
|  |  | 0 | 1309 | 280 | 96.4 | 61.5 | 23.6 | 88.3 |
|  |  | 0 | 4000 | 294 | 88.8 | 54.9 | 21.0 | 85.5 |
| 51 | F |  |  |  |  |  |  |  |
|  |  | 60 | 4000 | 294 | 88.4 | 54.6 | 21.0 | 85.5 |
|  |  | 90 | 4000 | 294 | 88.7 | 54.6 | 20.9 | 85.1 |
|  |  | 0 | 1309 | 300 | 96.7 | 64.3 | 27.0 | 94.4 |
|  |  | 0 | 4000 | 314 | 90.4 | 61.5 | 22.6 | 93.0 |
| 52 | G |  |  |  |  |  |  |  |
|  |  | 60 | 4000 | 314 | 90.2 | 61.3 | 22.4 | 92.8 |
|  |  | 90 | 4000 | 314 | 90.5 | 61.4 | 22.7 | 92.9 |
|  |  | 0 | 1309 | 279 | 92.1 | 60.5 | 22.9 | 90.5 |
|  |  | 0 | 4000 | 293 | 85.3 | 56.8 | 19.3 | 89.2 |
| 53 | H |  |  |  |  |  |  |  |
|  |  | 60 | 4000 | 293 | 85.2 | 56.9 | 19.1 | 89.2 |
|  |  | 90 | 4000 | 293 | 85.2 | 56.9 | 19.2 | 89.3 |
|  |  | 0 | 1309 | 309 | 94.8 | 64.6 | 22.0 | 91.3 |
|  |  | 0 | 4000 | 317 | 87.0 | 57.5 | 19.7 | 88.7 |
| 54 | I |  |  |  |  |  |  |  |
|  |  | 60 | 4000 | 317 | 87.1 | 57.4 | 19.7 | 88.5 |
|  |  | 90 | 4000 | 317 | 87.0 | 57.6 | 19.7 | 88.8 |
|  |  | 0 | 1309 | 314 | 92.0 | 60.0 | 21.6 | 88.7 |
|  |  | 0 | 4000 | 327 | 84.6 | 51.6 | 21.1 | 85.9 |
| 55 | J |  |  |  |  |  |  |  |

Table 7-continued

| Example | Catalyst | Reaction time (day) | SV (hr$^{-1}$) | Temperature of the nitrate bath (° C) | Conversion of acrolein (%) | Yield of acrylic acid (%) | Yield of methyl acrylate (%) | Selectivity of acrylic acid + methyl acrylate (%) |
| --- | --- | --- | --- | --- | --- | --- | --- | --- |
|  |  | 60 | 4000 | 327 | 84.4 | 51.7 | 20.6 | 85.7 |
|  |  | 90 | 4000 | 327 | 84.5 | 51.7 | 20.7 | 85.7 |
|  |  | 0 | 1309 | 330 | 88.7 | 53.5 | 18.4 | 81.1 |
| 56 | K | 0 | 4000 | 343 | 81.5 | 50.4 | 15.2 | 80.5 |
|  |  | 60 | 4000 | 343 | 81.6 | 50.5 | 15.0 | 80.3 |
|  |  | 90 | 4000 | 343 | 81.4 | 50.2 | 15.5 | 80.7 |

EXAMPLES 57 – 63

The reaction described in Example 33 was repeated in the presence of Catalyst A or G with a varying molar ratio between reagents in the gaseous feed mixture. The results are shown in Table 8.

In Table 8, gaseous feed mixtures T – Y have the following relative molar ratio:

| Gaseous feed mixture | methacrolein | methanol | oxygen | water vapor | nitrogen | phosphorus |
| --- | --- | --- | --- | --- | --- | --- |
| T | 1 | 1 | 2 | 2 | 16.1 | 14 × 10$^{-4}$ |
| U | 1 | 1 | 4 | 1 | 16.1 | 50 × 10$^{-4}$ |
| V | 1 | 1 | 4 | 6 | 16.1 | 50 × 10$^{-4}$ |
| W | 1 | 1 | 4 | 1 | 16.1 | 20 × 10$^{-3}$ |
| X | 1 | 1 | 4 | 1 | 16.1 | 3 × 10$^{-4}$ |
| Y | 1 | 2 | 4 | 0 | 16.1 | 14 × 10$^{-4}$ |

EXAMPLES 64 – 70

The reaction decribed in Example 46 was repeated in the presence of Catalyst A or G with a varying molar ratio between reagents in the gaseous feed mixture. The results are shown in Table 9.

In Table 9, gaseous feed mixtures $Z_1$ – $Z_6$ have the following relative molar ratio:

| Gaseous feed mixture | acrolein | methanol | oxygen | water vapor | nitrogen | phosphorus |
| --- | --- | --- | --- | --- | --- | --- |
| Z-1 | 1 | 1 | 4 | 6 | 16.1 | 14 × 10$^{-4}$ |
| Z-2 | 1 | 1 | 2 | 2 | 16.1 | 14 × 10$^{-4}$ |
| Z-3 | 1 | 1 | 4 | 6 | 16.1 | 50 × 10$^{-4}$ |
| Z-4 | 1 | 1 | 4 | 1 | 16.1 | 20 × 10$^{-3}$ |
| Z-5 | 1 | 1 | 4 | 6 | 16.1 | 3 × 10$^{-4}$ |
| Z-6 | 1 | 1 | 4 | 0 | 16.1 | 14 × 10$^{-4}$ |

Table 8

| Example | Catalyst | Gaseous feed mixture | Reaction time (day) | SV (hr$^{-1}$) | Temperature of the nitrate bath (° C) | Conversion of methacrolein (%) | Yield of methacrylic acid (%) | Yield of methyl methacrylate (%) | Selectivity of methacrylic acid + methyl methacrylate (%) |
| --- | --- | --- | --- | --- | --- | --- | --- | --- | --- |
| 57 | A | T | 0 | 1034 | 316 | 72.3 | 30.6 | 25.9 | 78.1 |
|  |  |  | 0 | 4000 | 331 | 67.6 | 28.4 | 23.8 | 77.2 |
|  |  |  | 90 | 4000 | 331 | 67.8 | 28.3 | 24.1 | 77.3 |
| 58 | A | U | 0 | 1034 | 299 | 73.5 | 29.3 | 32.8 | 84.5 |
|  |  |  | 0 | 4000 | 316 | 69.5 | 27.1 | 30.1 | 82.3 |
|  |  |  | 90 | 4000 | 316 | 69.3 | 27.3 | 29.8 | 82.4 |
| 59 | A | V | 0 | 1034 | 287 | 72.1 | 35.4 | 20.6 | 77.7 |
|  |  |  | 0 | 4000 | 299 | 68.6 | 30.2 | 22.1 | 76.2 |
|  |  |  | 90 | 4000 | 299 | 68.7 | 30.0 | 22.2 | 76.0 |
| 60 | A | W | 0 | 1034 | 301 | 73.9 | 30.1 | 31.1 | 82.8 |
|  |  |  | 0 | 4000 | 316 | 69.4 | 28.0 | 29.0 | 82.1 |
|  |  |  | 90 | 4000 | 316 | 69.5 | 27.9 | 30.1 | 81.9 |
| 61 | A | X | 0 | 1034 | 305 | 72.5 | 30.1 | 30.8 | 84.0 |
|  |  |  | 0 | 4000 | 320 | 68.3 | 27.6 | 27.3 | 81.9 |
|  |  |  | 90 | 4000 | 320 | 68.4 | 27.3 | 28.7 | 81.9 |
| 62 | A | Y | 0 | 1034 | 300 | 60.1 | 22.5 | 28.6 | 85.0 |
|  |  |  | 0 | 4000 | 316 | 56.0 | 21.0 | 26.1 | 84.1 |
|  |  |  | 90 | 4000 | 316 | 56.1 | 21.0 | 26.2 | 84.1 |
| 63 | G | Y | 0 | 1034 | 310 | 61.0 | 21.0 | 26.1 | 77.0 |
|  |  |  | 0 | 4000 | 314 | 55.2 | 19.2 | 22.9 | 76.2 |
|  |  |  | 90 | 4000 | 314 | 55.1 | 19.1 | 22.8 | 76.1 |

Table 9

| Example | Catalyst | Gaseous feed mixture | Reaction time (day) | SV (hr$^{-1}$) | Temperature of the nitrate bath (° C) | Conversion of acrolein (%) | Yield of acrylic acid (%) | Yield of methyl acrylate (%) | Selectivity of acrylic acid + methyl acrylate (%) |
| --- | --- | --- | --- | --- | --- | --- | --- | --- | --- |
| 64 | A | Z-1 | 0 | 1309 | 312 | 94.1 | 63.0 | 26.7 | 95.3 |
|  |  |  | 0 | 4000 | 324 | 89.2 | 60.5 | 23.2 | 93.8 |
|  |  |  | 90 | 4000 | 324 | 89.3 | 60.3 | 23.3 | 93.6 |
| 65 | A | Z-2 | 0 | 1309 | 328 | 91.8 | 60.0 | 26.3 | 94.0 |
|  |  |  | 0 | 4000 | 344 | 87.6 | 57.3 | 24.4 | 93.3 |
|  |  |  | 90 | 4000 | 344 | 87.5 | 57.5 | 24.2 | 93.4 |
| 66 | A | Z-3 | 0 | 1309 | 314 | 93.9 | 62.7 | 26.8 | 95.3 |
|  |  |  | 0 | 4000 | 326 | 89.2 | 60.2 | 23.7 | 94.0 |
|  |  |  | 90 | 4000 | 326 | 89.3 | 60.3 | 23.6 | 93.9 |
| 67 | A | Z-4 | 0 | 1309 | 299 | 96.4 | 63.3 | 29.0 | 95.7 |
|  |  |  | 0 | 4000 | 303 | 91.2 | 60.1 | 25.9 | 94.3 |
|  |  |  | 90 | 4000 | 303 | 91.1 | 60.0 | 26.1 | 94.5 |
| 68 | A | Z-5 | 0 | 1309 | 309 | 94.2 | 63.2 | 26.2 | 94.9 |
|  |  |  | 0 | 4000 | 324 | 89.0 | 60.3 | 22.9 | 93.5 |
|  |  |  | 90 | 4000 | 324 | 89.1 | 60.4 | 23.0 | 93.6 |
| 69 | A | Z-6 | 0 | 1309 | 301 | 89.7 | 61.0 | 26.6 | 97.8 |
|  |  |  | 0 | 4000 | 317 | 81.6 | 55.2 | 23.7 | 96.7 |
|  |  |  | 90 | 4000 | 317 | 81.7 | 55.2 | 23.9 | 96.8 |

Table 9-continued

| Example | Catalyst | Gaseous feed mixture | Reaction time (day) | SV (hr$^{-1}$) | Temperature of the nitrate bath (° C) | Conversion of acrolein (%) | Yield of acrylic acid (%) | Yield of methyl acrylate (%) | Selectivity of acrylic acid + methyl acrylate (%) |
|---|---|---|---|---|---|---|---|---|---|
|  |  |  | 0 | 1309 | 309 | 91.0 | 60.9 | 27.3 | 96.9 |
| 70 | G | Z - 6 | 0 | 4000 | 315 | 84.3 | 57.2 | 23.9 | 96.2 |
|  |  |  | 90 | 4000 | 315 | 84.4 | 57.4 | 23.9 | 96.3 |

EXAMPLE 71

The reaction described in Examples 34 – 43 was repeated except that metaphosphoric acid, pyrophosphoric acid, phosphorous acid, trimethyl phosphate and solid phosphoric acid were used in place of orthophosphoric acid, respectively.

The obtained results were comparable to those of Examples 34 – 43.

EXAMPLE 72

The reaction described in Examples 46 – 56 was repeated except that orthophosphoric acid, metaphosphoric acid, pyrophosphoric acid, phosphorous acid and solid phosphoric acid were used in place of trimethyl phosphate, respectively.

The obtained results are comparable to those of Examples 46 – 56.

What is claimed is:

1. A process for simultaneously producing methacrylic acid and a methacrylate or acrylic acid and an acrylate, which process comprises reacting methacrolein or acrolein with an aliphatic alcohol and molecular oxygen in vapor phase in the presence of a catalyst consisting essentially of (1) palladium, (2) phosphorous and (3) oxygen as essential elements and (4) antimony as an optional element.

2. The process as claimed in claim 1 wherein a phosphoric acid or a phosphorus compound capable of forming a phosphoric acid through chemical change during the reaction is concurrently supplied to the reaction system.

3. The process as claimed in claim 1 wherein said catalyst is a composition represented by the following formula:

$$Pd_aP_bSb_cO_d$$

wherein letters a, b, c and d represent numbers of palladium, phosphorus, antimony and oxygen atoms, respectively, when a is 1, b is 1 to 42, c is 0 to 15 and d is a number which is of itself determined by total valences of other elements, generally from 3.5 to 115.

4. The process as claimed in claim 3 wherein a is 1, b is 1 to 28, c is 0.2 to 10 and d is 3.8 to 85.

5. The process as claimed in claim 1 wherein said aliphatic alcohol is methanol.

6. The process as claimed in claim 2 wherein said phosphoric acid is orthophosphoric acid.

7. The process as claimed in claim 2 wherein said phosphoric acid is pyrophosphoric acid.

8. The process as claimed in claim 2 wherein said phosphoric acid is metaphosphoric acid.

9. The process as claimed in claim 2 wherein said phosphorus compound capable of forming a phosphoric acid through chemical change during the reaction is an organic phosphoric acid.

10. The process as claimed in claim 2 wherein said phosphorus compound capable of forming a phosphoric acid through chemical change during the reaction is a solid phosphoric acid.

11. The process as claimed in claim 1 wherein a reagent is methacrolein.

12. The process as claimed in claim 1 wherein a reagent is acrolein.

* * * * *